(12) United States Patent
Matsushita et al.

(10) Patent No.: US 10,688,120 B2
(45) Date of Patent: Jun. 23, 2020

(54) ALLERGY VACCINE COMPOSITION

(71) Applicant: NITTO DENKO CORPORATION, Osaka (JP)

(72) Inventors: Kyohei Matsushita, Osaka (JP); Masahiro Fukasaka, Osaka (JP); Takuya Shishido, Osaka (JP); Daisuke Asari, Osaka (JP); Katsuyuki Okubo, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/570,851

(22) PCT Filed: Apr. 28, 2016

(86) PCT No.: PCT/JP2016/063395
§ 371 (c)(1),
(2) Date: Oct. 31, 2017

(87) PCT Pub. No.: WO2016/178410
PCT Pub. Date: Nov. 10, 2016

(65) Prior Publication Data
US 2018/0147235 A1   May 31, 2018

(30) Foreign Application Priority Data
May 1, 2015   (JP) ................... 2015-094304

(51) Int. Cl.

| A61K 31/739 | (2006.01) |
| A61K 39/39 | (2006.01) |
| A61K 39/00 | (2006.01) |
| A61K 39/02 | (2006.01) |
| A61K 39/35 | (2006.01) |
| A61P 37/02 | (2006.01) |
| A61P 37/08 | (2006.01) |
| A61P 11/02 | (2006.01) |
| A61P 11/06 | (2006.01) |

(52) U.S. Cl.
CPC ............ *A61K 31/739* (2013.01); *A61K 39/02* (2013.01); *A61K 39/35* (2013.01); *A61K 39/39* (2013.01); *A61P 11/02* (2018.01); *A61P 11/06* (2018.01); *A61P 37/02* (2018.01); *A61P 37/08* (2018.01); *A61K 2039/55572* (2013.01); *A61K 2039/55594* (2013.01)

(58) Field of Classification Search
CPC ...... A61K 31/739; A61K 39/02; A61K 39/35; A61K 36/03; A61K 36/48; A61K 36/88; A61K 36/899; A61K 2039/55572; A61K 2039/55594; A61K 39/39; A61P 11/02; A61P 11/06; A61P 17/04; A61P 37/02; A61P 37/08; A23V 2002/00; A23V 2200/324; A23V 2250/21; A23L 11/09; A23L 33/105; A23L 7/104; C12N 1/20; C12P 19/04; C12P 1/04; G06F 19/00; G06F 19/28; G16H 10/40; G16H 20/60; Y02P 60/877; G01N 33/497
See application file for complete search history.

(56) References Cited

U.S. PATENT DOCUMENTS

| 4,939,239 A | 7/1990 | Matsuhashi et al. |
| 2013/0266612 A1 | 10/2013 | Fukasaka et al. |

FOREIGN PATENT DOCUMENTS

| EP | 0416816 A1 | 3/1991 |
| EP | 1 961 823 A1 | 8/2008 |
| JP | H01156926 A | 6/1989 |
| JP | 2000510844 A | 8/2000 |
| JP | 2009242367 A | 10/2009 |
| JP | 2013231026 A | 11/2013 |
| WO | 9742947 A1 | 11/1997 |
| WO | 2006095289 A1 | 9/2006 |

OTHER PUBLICATIONS

Nakata et al. Food Sci. Nutrition 2: 638-646, Online pub 2014.*
Savill P. Quarterly J. Forestry 109: 97-102, 2015.*
Kohchi et al. J. Biosci. Bioeng. 102: 485-496, 2006.*
Yoshida et al. Anticancer Res. 29: 4867-4870, 2009.*
International Search Report from Application No. PCT/JP2016/063395 dated Jul. 13, 2016.
International Preliminary Report on Patentability from Application No. PCT/JP2016/063395 dated Nov. 7, 2017.

(Continued)

*Primary Examiner* — Sarvamangala Devi
(74) *Attorney, Agent, or Firm* — Greenblum & Bernstein, P.L.C.

(57) ABSTRACT

The present invention provides an allergy vaccine composition that is useful as a prophylactic or therapeutic agent for an allergic disease and can safely and effectively induce immune tolerance. The vaccine composition is to be administered to a human or animal with an allergic disease for the prevention or treatment of the allergic disease. The vaccine composition contains: an immunomodulator which is a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas*, and *Enterobacter*, or a salt of the lipopolysaccharide; and at least one allergen.

9 Claims, No Drawings

(56) References Cited

OTHER PUBLICATIONS

Yufa Wang et al., "Neonatal exposure with LPS and/or allergen prevents experimental allergic airways disease: Development of tolerance using environmental antigens", Environmental and occupational respiratory disorders, 2006, pp. 143-151, vol. 118, J Allergy Clin Immunol.
Hiroyuki Inagawa et al., "Inhibitory Effect by Intradermal Administration of Pantoea Aggolomerans LPS (LPSp) and Oral Administration of ONO-4007, A Lipid A Derivative, on IgE-Mediated Allergy Reaction", 1997, pp. 464-466, vol. 11(3), 1997, Biotherapy.
Extended European Search Report for EP 16 78 9546.5, dated Nov. 28, 2018.
Office Action for JP App. No. 2016-091051 dated Mar. 3, 2020 (w/ translation).
Office Action for EP App. No. 16789546.5 dated Mar. 19, 2020.

\* cited by examiner

ALLERGY VACCINE COMPOSITION

TECHNICAL FIELD

The present invention relates to allergy vaccine compositions useful as prophylactic or therapeutic agents for allergic diseases. In particular, the present invention relates to an allergy vaccine composition that contains a specific lipopolysaccharide as an immunomodulator together with an allergen and is capable of safely and effectively mitigating allergic symptoms when administered.

BACKGROUND ART

Current therapy for allergic diseases is symptomatic therapy using an antihistamine in most cases, and hyposensitization therapy is drawing attention as potential radical therapy for allergic diseases.

The hyposensitization therapy usually requires long-term administration of a drug for about two to three years, and thus there seems to be a demand for an effective, easy-to-handle vaccine formulation that can improve the quality of life (QOL) of caregivers and patients.

Vaccine formulations are divided into those aiming to induce an immune response by vaccination and those aiming to induce immune tolerance by vaccination. With regard to the former induction of an immune response, Patent Literature 1 discloses a case where transnasal administration of a *Pantoea*-derived LPS (Immuno potentiator from *Pantoea agglomerans* 1), which is a lipopolysaccharide derived from *Pantoea* bacteria, together with an antigen induced an immune response. Patent Literature 2 discloses a case where oral administration of a vaccine formulation containing a *Pantoea*-derived LPS sufficiently induced an immune response.

Nevertheless, there is no case demonstrating the latter induction of immune tolerance with a vaccine formulation containing a *Pantoea*-derived LPS. In other words, there is no disclosure demonstrating whether multiple administration of a vaccine formulation containing a *Pantoea*-derived LPS can mitigate allergic symptoms.

CITATION LIST

Patent Literature

Patent Literature 1: JP 2009-242367 A
Patent Literature 2: JP 2013-231026 A

SUMMARY OF INVENTION

Technical Problem

The present invention aims to provide an allergy vaccine composition which is safe, usable as a prophylactic or therapeutic agent for an allergic disease, and capable of effectively inducing immune tolerance.

Solution to Problem

As a result of intensive studies to solve the above problem, the present inventors have found out that administration of a lipopolysaccharide derived from a specific gram-negative bacterium or a salt thereof as an immunomodulator together with an allergen enables safe, effective induction of immune tolerance. The present invention was thus completed.

The present invention relates to a vaccine composition to be administered to a human or animal with an allergic disease for the prevention or treatment of the allergic disease, the vaccine composition containing: an immunomodulator which is a lipopolysaccharide derived from at least one gram-negative bacterium selected from the group consisting of *Serratia, Leclercia, Rahnella, Acidicaldus, Acidiphilium, Acidisphaera, Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pseudomonas, Achromobacter, Bacillus, Methanoculleus, Methanosarcina, Clostridium, Micrococcus, Flavobacterium, Pantoea, Acetobacter, Zymomonas, Xanthomonas*, and *Enterobacter*, or a salt thereof; and at least one allergen.

In the allergy vaccine composition of the present invention, the immunomodulator and the allergen preferably satisfy a mass ratio (total mass of immunomodulator/total mass of allergen) of 0.002 to 500.

If the ratio is lower than 0.002, the intensity of immune tolerance induced may be insufficient. If the ratio is higher than 500, a safety problem may arise. The lower limit of the mass ratio of the immunomodulator to the allergen is more preferably 0.01, and the upper limit thereof is more preferably 100. The immunomodulator and the allergen in a mass ratio within the above range enable induction of immune tolerance with sufficient intensity and ensure the safety. The upper limit of the mass ratio of the immunomodulator to the allergen is still more preferably 10.

The "mass of the allergen" as used herein means the mass of an allergen protein contained in the allergen in the vaccine, unless otherwise specified. In the case of an allergen that is a vivo-derived substance, the "mass of the allergen" means the mass of all the proteins contained in the allergen.

The allergy vaccine composition of the present invention is preferably to be administered to a human or animal five or more times.

The present invention also preferably relates to a method for treating an allergic disease wherein the allergy vaccine composition is administered to a human or animal with the allergic disease five or more times.

The present invention also preferably relates to the allergy vaccine composition for the use as a prophylactic or therapeutic agent for an allergic disease caused by an allergen.

The term "allergen" as used herein means an antigen that specifically reacts with an antibody from a human or animal with an allergic disease, and is typically a protein.

Specific examples of the allergen include allergens derived from pollens of any tree (e.g., Acacia, Alder, Ash, Beech American, Birch, Box Elder, Cedar Mountain, Cedar Red, Cottonwood, Japanese Cypress, Elm American, Elm Chinese, Japanese Douglas fir, Sweetgum, *Eucalyptus*, Hackberry, Hickory, Linden, Maple Sugar, Mesquite, Mulberry, Oak, Olive, Pecan, Pepper Tree, Pine, Privet, Olive Russian, Sycamore American, Tree of Heaven, Walnut, and Willow Black); allergens derived from pollens of any grasses (e.g., Cotton plant, Bermuda, Kentucky Blue, Smooth Brome, Cultivated Corn, Meadow Fescue, Johnson, Cultivated Oats, Orchard, Red top, Rye Perennial, Rice, Sweet Vernal, Timothy, Carelessweed, *Chenopodium*, Cocklebur, Dock Sorrel, Goldenrod, *Kochia*, Lambs Quarters, Marigold, Nettle, Pigweed Rough, Plantain English, Ragweed Tall, Ragweed, Ragweed Western, Russian Thistle, Sagebrush Common, Scotch bloom, and Sheep Sorrel); allergens derived from any bugs (e.g., silkworm, mite, honeybee, wasp, ant, and cockroach); allergens derived from any bacteria (e.g., *Alternaria tenuis, Aspergillus fumigatus, Botrytis cinerea, Candida albicans, Cephalosporium acremonium, Curvularia spicifera, Epicoccum nigrum, Epidermophyton floccosum, Fusarium vasinfectum, Helminthosporium interseminatum, Hormodendrum cladosporioides, Mucor rasemosus, Penicillium notatum, Phoma herbarium, Pullularia pullulans,* and *Rhizopus nigricans*); allergens derived from body hairs of any animals (e.g., Dog, Cat, and Bird); allergen proteins derived from house dust; and allergens derived from any foods (e.g., OVA). The allergen may be any antigen that specifically reacts with an antibody from a human with an allergic disease.

The term "allergic disease" as used herein means any disease involving an immune reaction against the allergen. Typical examples of the allergic disease include atopic dermatitis, allergic rhinitis (e.g., hay fever), allergic conjunctivitis, allergic gastroenteritis, bronchial asthma, infantile asthma, food allergies, drug allergies, and urticaria.

In the allergy vaccine composition of the present invention, the allergen has only to be contained in an effective amount. For example, the allergen is preferably contained in an amount in the range of 0.01 to 10000 μg per single dose in the allergy vaccine composition of the present invention. If the allergen content is less than 0.01 μg, the function of the composition as a prophylactic or therapeutic agent for an allergic disease may be insufficient. If the allergen content is more than 10000 μg, a safety problem may arise. The lower limit of the allergen content is more preferably 0.1 μg, and the upper limit thereof is more preferably 5000 μg.

The allergy vaccine composition of the present invention contains an immunomodulator.

The immunomodulator may be a toll-like receptor 4 (TLR4) agonist. In the present invention, a specific lipopolysaccharide is used as the toll-like receptor 4 (TLR4) agonist.

The "lipopolysaccharide" as used herein may be a lipopolysaccharide itself or a derivative thereof as long as it has the properties of the lipopolysaccharide. The salt as used herein may be any organic acid salt or inorganic acid salt, and is preferably a pharmaceutically acceptable salt.

The lipopolysaccharide (hereinafter, also referred to as LPS) is described hereinbelow.

The LPS is a composite compound composed of a lipid and a saccharide existing in the outer membranes surrounding peptide glycan of cell walls of gram-negative bacteria such as *Escherichia coli, Salmonella typhimurium,* and *Bordetella pertussis,* and is known as an active component of O antigen and endotoxin (J. M. Ghuysen and R. Hakenbeck ed., "New Comprehensive Biochemistry", Vol. 27, Bacterial Cell Wall, p. 18, Elsevea, 1994).

The basic structure of the LPS consists of three components: lipid A having a specific lipid; an oligosaccharide covalently bonded thereto, which is called an R core; and an O-specific polysaccharide ("Nikkei Biotechnology Up-to-date Glossary", P. 431, Nikkei Macgraw-hill Co., 1985).

The structure of the O-specific polysaccharide has the most variations among the components, is specific to bacterial species, and shows the activity as known as O-antigen. It is generally characterized by a repeating structure of oligosaccharides composed of several species of monosaccharides. Also known are those composed of a single species of monosaccharide and those having no repeating structure.

The allergy vaccine composition of the present invention contains a lipopolysaccharide derived from a specific gram-negative bacterium or a salt thereof as the immunomodulator. Such a lipopolysaccharide or a salt thereof is contained in many food items, and hence assured to be safe for the living body. Extracts derived therefrom or modified substances thereof can also be used as they are.

Examples of the bacterium from which a lipopolysaccharide for the use as the immunomodulator is derived include *Serratia* (species closely related to *Pantoea*; bread, meat, milk, one species of indigenous bacteria), *Leclercia* (species closely related to *Pantoea*; food as a whole (soil bacteria)), *Rahnella* (species closely related to *Pantoea*; one species of indigenous bacteria), *Acidicaldus* (acetic acid bacteria; production of fermented foods), *Acidiphilium* (acetic acid bacteria; production of fermented foods), *Acidisphaera* (acetic acid bacteria; production of fermented foods), *Acidocella* (acetic acid bacteria; production of fermented foods), *Acidomonas* (acetic acid bacteria; production of fermented foods), *Asaia* (acetic acid bacteria; production of fermented foods), *Belnapia* (acetic acid bacteria; production of fermented foods), *Craurococcus* (acetic acid bacteria; production of fermented foods), *Gluconacetobacter* (acetic acid bacteria; production of fermented foods), *Gluconobacter* (acetic acid bacteria; production of fermented foods), *Kozakia* (acetic acid bacteria; production of fermented foods), *Leahibacter* (acetic acid bacteria; production of fermented foods), *Muricoccus* (acetic acid bacteria; production of fermented foods), *Neoasaia* (acetic acid bacteria; production of fermented foods), *Oleomonas* (acetic acid bacteria; production of fermented foods), *Paracraurococcus* (acetic acid bacteria; production of fermented foods), *Rhodopila* (acetic acid bacteria; production of fermented foods), *Roseococcus* (acetic acid bacteria; production of fermented foods), *Rubritepida* (acetic acid bacteria; production of fermented foods), *Saccharibacter* (acetic acid bacteria; production of fermented foods), *Stella* (acetic acid bacteria; production of fermented foods), *Swaminathania* (acetic acid bacteria; production of fermented foods), *Teichococcus* (acetic acid bacteria; production of fermented foods), *Zavarzinia* (acetic acid bacteria; production of fermented foods), *Pseudomonas* (*Pseudomonas* bacteria; beef, egg, meat, fish, vegetable), *Achromobacter* (*Achromobacter* bacteria; fish, meat), *Bacillus* (*Bacillus* bacteria; rice, vegetable), *Methanoculleus* (methane-producing bacteria; methane-producing bacteria parasitizing on animal intestines), *Methanosarcina* (methane-producing bacteria; methane-producing bacteria parasitizing on animal intestines), *Clostridium* (*Clostridium* bacteria; meat, milk, vegetable, canned food), *Micrococcus* (Actinomycetes; meat, fish), *Flavobacterium* (*Bacteroides* bacteria; putrefactive bacteria of food), *Pantoea, Acetobacter, Zymomonas, Xanthomonas,* and *Enterobacter.* These bacteria are contained in many food items or used in the food production process, and hence they are assured to be safe for the living body.

Preferred among these is at least one selected from the group consisting of *Serratia, Leclercia, Rahnella, Acidicaldus, Acidiphilium, Acidisphaera Acidocella, Acidomonas, Asaia, Belnapia, Craurococcus, Gluconacetobacter, Gluconobacter, Kozakia, Leahibacter, Muricoccus, Neoasaia, Oleomonas, Paracraurococcus, Rhodopila, Roseococcus, Rubritepida, Saccharibacter, Stella, Swaminathania, Teichococcus, Zavarzinia, Pantoea, Acetobacter, Zymomonas, Xanthomonas,* and *Enterobacter*. The gram-negative bacterium is at least one selected from the group consisting of *Pantoea, Acetobacter, Zymomonas, Xanthomonas,* and *Enterobacter*. In particular, lipopolysaccharides derived from *Pantoea* are currently used as health food, and are more effective especially when they are administered to mucosal surfaces. Extracts derived from these bacteria or modified substances thereof can also be used as they are.

The lipopolysaccharide derived from a gram-negative bacterium or a salt thereof needs to be used with consideration for the safety for the living body, and can be used after being modified for detoxification.

The toll-like receptor 4 (TLR4) agonist may be a derivative of the above specific lipopolysaccharide, such as lipid A obtained by removing the polysaccharide moiety, monophosphoryl lipid A, or 3-deacylated MPL. The agonist may alternatively be a salt.

The lipid A obtained by removing the polysaccharide moiety of a lipopolysaccharide has only to be an isolate derived from any of the above specific gram-negative bacterium, or may be a synthetic product having the same structure as the corresponding isolate derived from the gram-negative bacterium.

Monophosphoryl lipid (MPL) obtained by dephosphorylation of the lipid A or a salt thereof may also favorably be used as a modified substance of the lipid A. The monophosphoryl lipid as used herein may be monophosphoryl lipid itself, or may be a derivative thereof as long as the properties of the monophosphoryl lipid are possessed. In particular, 3-deacylated monophosphoryl lipid (3D-MPL) that has already been actually used as an immunostimulant in the medical field or a synthetic glucopyranosyl lipid that is not deacylated, proposed in US 2010/0310602, is preferred from the viewpoint of the safety for the living body.

Also, the monophosphoryl lipid may preferably be any of those derived from *Salmonella* which are safe and have been used in the past.

In the present invention, a LPS derived from *Pantoea agglomerans* is preferably used. In particular, the LPS derived from *Pantoea agglomerans* preferably has a molecular weight of 5000±3000, preferably 5000±2000, determined by SDS-PAGE using a protein marker. The molecular weight as used herein is measured by the position of a stained band by SDS-PAGE using a protein marker, and the details will be described later.

The LPS derived from *Pantoea agglomerans* as preferably used in the present invention is a lipopolysaccharide characterized in that the O-antigen moiety has a repeating structure of rhamnose and glucose.

The LPS derived from *Pantoea agglomerans* can be produced by culturing *Pantoea agglomerans* according to an ordinary method, collecting the bacterial cells from the culture medium, and purifying the collected bacterial cells according to a known method.

The molecular weight of the LPS derived from *Pantoea agglomerans* can be measured by the following method.

That is, for a LPS derived from *Pantoea agglomerans* prepared as a blend or for a LPS derived from *Pantoea agglomerans* extracted and purified from a vaccine composition by an appropriate method, the molecular weight can be determined by the following method.

A LPS derived from *Pantoea agglomerans* is dissolved in distilled water to prepare a 1 mg/mL solution, and the solution and Sample buffer solution 2ME+ (Wako Pure Chemical Industries, Ltd.) are mixed in equal amounts. The resulting mixture is dipped in a boiling water bath for five minutes, and then immediately dipped in ice water to be rapidly cooled.

A slab gel electrophoresis tank (Marisol) is filled with a running buffer (Atto Corp.), and 20% polyacrylamide gel is fixed in the electrophoresis tank. A 10-µL portion of a sample is put into each sample groove, and an electric current is supplied for at least one hour at a voltage of 100 V and the electrophoresis is continued until the pigment is eluted from the gel. After completion of the electrophoresis, silver staining is performed with a silver staining kit 161-0443 (Bio-Rad Laboratories, Inc.) at room temperature, and the behavior is checked.

The allergy vaccine composition of the present invention may also contain a different known immunomodulator as long as it contains a lipopolysaccharide derived from a specific gram-negative bacterium or a salt thereof as the aforementioned immunomodulator.

The allergy vaccine composition of the present invention can be prepared by blending the aforementioned allergen and immunomodulator with other ingredients (e.g., phosphate buffer solution) as needed, and stir-mixing them by a known method, and further heating, cooling, or non-heat drying the mixture as needed by a known method.

The allergy vaccine composition of the present invention may contain an additive as needed. Examples of the additive include, in accordance with factors such as the compatibility with the above allergen and immunomodulator and the intended dosage regimen, vehicles, binders, fragrance materials, flavoring substances, sweeteners, colorants, tonicity agents, antiseptic and antimicrobial agents, antioxidants, solubilizers, dissolution aids, suspending agents, fillers, pH modifiers, stabilizers, absorption promoters, release-control agents, plasticizers, crosslinkers, adhesive, and surfactants. These additives may be used alone or in combination of two or more.

These additives may be produced from any materials, and known materials can be used.

The allergy vaccine composition of the present invention may be in any dosage form, such as a liquid for external use (e.g., a liquid, an emulsion, a spray, a semi-solid preparation, a solid preparation, a liniment, or a lotion), a spray for external use (e.g., an aerosol), a gel, a patch (e.g., a tape or a poultice), an ointment, a plaster, or a cream. The categories, definitions, properties, production processes, and others of these formulations are well known in the technical field. For example, see the Japanese Pharmacopeia, 16th Edition.

As will be mentioned later, the allergy vaccine composition of the present invention in the dosage form of a liquid, an emulsion, or a solid preparation, which is to be mixed with liquid so as to be dissolved, emulsified, or suspended for the use, can suitably be administered by injection to a human or animal. The allergy vaccine composition of the present invention in the dosage form of a liquid, a spray, a semi-solid preparation, or a solid preparation can suitably be administered to a mucous membrane of a human or animal. The allergy vaccine composition of the present invention in the dosage form of a liquid for external use (e.g., a liniment or a lotion), a spray for external use (e.g., an aerosol), a gel, a patch (e.g., a tape or a poultice), an ointment, a plaster, or a cream can suitably be administered to the skin of a human or animal.

The allergy vaccine composition of the present invention is used for inducing immune tolerance. The immune tolerance-inducing effect may be quantitatively determined by any method and various methods have been developed. For example, the effect can be determined by an immune tolerance induction test using an animal model for immunological evaluation and ELISA (allergen-specific IgE antibody). An example of a sample for determining the immune tolerance may be the blood of an animal model for immunological evaluation.

The term "subject" as used herein means any of the animals to which the allergy vaccine composition can be administered for induction of immune tolerance at a practical stage, and typically means any of mammals, including human, such as mice, rats, dogs, cats, horses, cows, sheep, pigs, goats, monkeys, and chimpanzees. The subject is particularly preferably a human.

The allergy vaccine composition of the present invention preferably satisfies a specific combination of the type of the antigen and the route of administration. Specifically, transdermal administration is preferred for OVA as the antigen; sublingual administration or transdermal administration is preferred for cedar pollen as the antigen; and subcutaneous injection is preferred for mite allergen as the antigen.

<Allergy Vaccine Composition for Injection>

The allergy vaccine composition for injection is preferably in the dosage form of a liquid, an emulsion, a water-soluble or hydrophobic suspension, or a semi-solid or solid preparation which is to be mixed with liquid so as to be dissolved or suspended for the use. Any dosage form with a certain degree of liquidity enables suitable injection to a human or animal.

These dosage forms can be prepared from any material, and known materials can be used.

The allergen and the immunomodulator may be contained in any amount in the allergy vaccine composition for injection. For example, the allergen is preferably contained in an amount within the range of 0.01 to 10000 µg, more preferably within the range of 0.1 to 5000 µg, in the allergy vaccine composition for injection. The immunomodulator is preferably contained in the allergy vaccine composition for injection such that the mass ratio thereof to the allergen (in other words, total mass of immunomodulator/total mass of allergen) falls, for example, within the range of 0.002 to 500, more preferably within the range of 0.002 to 50, still more preferably within the range of 0.01 to 10.

The immunomodulator is preferably a *Pantoea*-derived LPS.

The vaccine composition of the present invention for injection may be administered by any method, and is preferably administered by any of intradermal injection, subcutaneous injection, and intramuscular injection.

<Allergy Vaccine Composition for Transmucosal Administration>

Examples of the transmucosal administration include administration to nasal mucosa, oral mucosa, ocular mucosa, ear mucosa, genital mucosa, pharyngeal mucosa, tracheal mucosa, bronchial mucosa, pulmonary mucosa, gastric mucosa, intestinal mucosa, or rectal mucosa.

The allergy vaccine composition for transmucosal administration may be in the dosage form of, for example, a semi-solid preparation such as gel (jelly), cream, ointment, or plaster; a liquid; a solid preparation such as powder, fine granules, granules, a film, a tablet, or an orally disintegrating tablet; a semi-solid preparation; a spray for mucosa such as aerosol; or an aspirating preparation. The categories, definitions, properties, production processes, and others of these formulations are well known in the technical field. For example, see the Japanese Pharmacopoeia, 16th Edition.

The allergy vaccine composition of the present invention for transmucosal administration is administered to a mucosa of a human or animal, and thus the above semi-solid preparations and solid preparations are preferably dissolved by body fluids and/or body temperature.

These dosage forms can be prepared from any material, and known materials can be used.

The allergen and the immunomodulator may be contained in any amount in the allergy vaccine composition for transmucosal administration. For example, the allergen is preferably contained in an amount within the range of 0.01 to 10000 µg, more preferably within the range of 0.1 to 5000 µg, in the allergy vaccine composition for transmucosal administration. The immunomodulator is preferably contained in the allergy vaccine composition for transmucosal administration such that the mass ratio thereof to the allergen (in other words, total mass of immunomodulator/total mass of allergen) falls, for example, within the range of 0.002 to 500, more preferably within the range of 0.01 to 100.

The immunomodulator contained in the allergy vaccine composition for transmucosal administration is preferably a *Pantoea*-derived LPS. For the allergy vaccine composition for transmucosal administration which is to be transnasally administered, the dosage form thereof is preferably a solution or dry powder containing an allergen and a *Pantoea*-derived LPS. The allergy vaccine composition for transnasal administration which is in the form of the above solution may be prepared as a solution in advance, or may be dissolved or dispersed in a liquid, such as a physiological saline solution, in use. For the allergy vaccine composition for transmucosal administration which is to be sublingually administered, the dosage form thereof is preferably a liquid, semi-solid preparation, or solid preparation containing an allergen and a *Pantoea*-derived LPS. The allergy vaccine composition for sublingual administration which is in the form of the above solution may be prepared as a solution in advance, or may be dissolved or dispersed in a liquid, such as a physiological saline solution, in use.

<Allergy Vaccine Composition for Transdermal Administration>

The vaccine pharmaceutical composition for transdermal administration may be in the dosage form of, for example, a liquid for external use such as a liniment or a lotion, a spray for external use such as an aerosol, a gel, a patch such as a tape or a poultice, an ointment, a plaster, or a cream. The categories, definitions, properties, production processes, and others of these formulations are well known in the technical field. For example, see the Japanese Pharmacopoeia, 16th Edition. From the viewpoint of compliance, the dosage form of the allergy vaccine composition for transdermal administration is particularly preferably a patch (e.g., a tape or a poultice).

These dosage forms can be prepared from any material, and known materials can be used.

The allergen and the immunomodulator may be contained in any amount in the allergy vaccine composition for transdermal administration (in an adhesive layer in the case of a tape). The amount of the allergen is preferably 0.01 to 40 wt %, more preferably 0.1 to 30 wt %. The immunomodulator is preferably contained in the allergy vaccine composition for transdermal administration such that the mass ratio thereof to the allergen (in other words, total mass of immunomodulator/total mass of allergen) falls, for example, within the range of 0.002 to 500, more preferably within the range of 0.01 to 100.

The tape preferably includes an adhesive layer containing ingredients (i.e., the allergen, the immunomodulator, and the like), and a support that supports the adhesive layer. The tape may further include a release liner that prevents exposure of the adhesive layer before use and can be easily removed from the adhesive layer at the time of use.

Any adhesive may be used to form the adhesive layer. Preferred is a hydrophilic base such as sodium polyacrylate because it can favorably diffuse and release the allergen.

The adhesive may be contained in the adhesive layer in any amount. The amount thereof in terms of solid content is preferably 10 to 99 wt %, more preferably 20 to 95 wt % of the total weight of the adhesive layer.

The adhesive layer may have any thickness. Preferably, the thickness is 10 to 1000 µm. With the thickness within the above range, the adhesive layer can readily contain the ingredients each in an effective amount and exhibit sufficient adhesion. Moreover, the adhesive layer with such a thickness can be readily formed.

The support may be any one, and is preferably one substantially impermeable to the above ingredients. In other words, the support is preferably one that prevents passing of the ingredients such as the allergen and the immunomodulator contained in the adhesive layer through the support and an escape thereof from the back side, thereby preventing a decrease in the amounts of the ingredients.

In administration of the allergy vaccine composition of the present invention to a subject, the therapeutically effective amount for an allergic disease may widely vary depending on the severity of the disease, the age and relative health of the subject, and other known factors. In general, about 0.1 µg to 10 g/kg weight per day of the allergy vaccine composition will produce satisfactory results. The immunomodulator is administered either simultaneously with the allergen or successively, and is preferably administered simultaneously.

The therapeutically effective amount of the immunomodulator may widely vary depending on factors such as the specific type of the immunomodulator used and the presence of any other additives. In general, about 0.1 μg to 10 g/kg weight per day of the immunomodulator will produce satisfactory results.

The above daily dose may be administered once, or may be administered in multiple times, such as two or more times (e.g., two, three, four, five, or more times). The duration of each administration is preferably selected from the range of 1 minute to 7 days as appropriate. The administration interval is preferably selected from the range of every day to once a year (e.g., once a day, every other day, every third day, once a week, every other week, once a month, every third month, every half year, once a year) or longer depending on factors such as the conditions of the patient, the severity of the allergy disease, and the purpose of administration (i.e., therapeutic or prophylactic). For the therapeutic purpose for a patient actually with a severe disease, the allergy vaccine composition of the present invention is usually administered with greater frequency and/or a higher dose. For the prophylactic purpose for a patient without a disease, the allergy vaccine composition of the present invention is preferably administered with less frequency and/or a lower dose.

Advantageous Effects of Invention

The allergy vaccine composition of the present invention is a combination of at least one allergen with the aforementioned specific immunomodulator, and thus can more effectively induce immune tolerance when administered in the body and to the body surface.

When the allergy vaccine composition of the present invention in a dosage form for mucosal administration or transdermal administration is used for hyposensitization therapy, patients can self-administer the allergen protein at home and caregivers can easily administer the allergen protein. This significantly improves the QOL of the patients and the caregivers. Further, this vaccine composition can noninvasively be administered to the body surface. This provides excellent compliance.

In other words, the vaccine composition of the present invention can mitigate the problems relating to the QOL of patients, such as pain, fear, injection scars and subsequent cicatrization, and, in the case of repetitive administration, a burden on the patients' lives due to hospital visits.

The allergy vaccine composition of the present invention in the dosage form of a patch, such as a tape or a poultice, is advantageous in that the drug can reliably be administered at a predetermined dose; the drug release rate can be controlled at any rate; and the drug is prevented from being attached to sites other than the intended site. In addition, since a patch is easily detachable, it is advantageous in that patients can immediately discontinue the administration on their own by removing the patch from the site of application in case of any adverse effects, for example. Thus, a patch is particularly preferred from the viewpoint of compliance.

Administration of the allergy vaccine composition of the present invention significantly improves the effect of inducing immune tolerance compared to administration of the allergen alone. Further, noninvasive administration of the allergy vaccine composition of the present invention to the body surface (e.g., transdermal administration or transmucosal administration) induces strong immune tolerance compared to injection.

DESCRIPTION OF EMBODIMENTS

The present invention is specifically described with reference to, but not limited to, the following examples.

Examples 1 to 4, Comparative Examples 1 to 4

The preparations were prepared in amounts for five subjects per administration group.

OVA (Sigma-Aldrich, 10 μg/mL) and a solution of a *Pantoea agglomerans*-derived lipopolysaccharide (Macrophi Inc., 1 μg/mL) were mixed with a physiological saline solution to provide a vaccine composition as shown in Table 1 (for sublingual administration, transnasal administration, or subcutaneous administration).

Separately, the OVA (100 μg/mL) and the *Pantoea agglomerans*-derived lipopolysaccharide solution (10 μg/mL) were mixed with sodium polyacrylate (1000 μg), which serves as adhesive, to provide a drug-containing adhesive solution. This drug-containing adhesive solution was spread onto a polyester release film and dried to provide a drug-containing adhesive layer having a thickness of about 60 μm. This layer was transferred to a PET/nonwoven fabric laminated support having a thickness of 20 μm. Thereby, a film having a thickness of about 80 μm was obtained. The resulting film was cut into a size of 0.7 cm$^2$ to provide a vaccine composition (for transdermal administration) as shown in Table 1. In the comparative examples, the immunomodulator was not added and the allergen alone was mixed with a physiological saline solution or sodium polyacrylate which serves as adhesive. Thereby, a composition was prepared such that the amount of the allergen corresponds to the dose as shown in Table 1.

In Reference Examples 1 to 3, the mouse IgE with neither allergen nor immunomodulator added thereto was subjected to the measurement.

Five mice (8-week-old female BALB/C mice, Japan SLC, Inc.) per group were anesthetized and received the vaccine composition prepared in an amount of 20 μL for the sublingual administration group, 10 μL for the transnasal administration group, 200 μL for the subcutaneous injection group, or one tape for the transdermal administration group. The preparations were prepared such that the OVA (10 μg/mL) and the *Pantoea agglomerans*-derived lipopolysaccharide solution (1 μg/mL) were administered per administration. Within two weeks from the above administration, each mouse was anesthetized and received the vaccine composition in an amount of 20 μL for the sublingual administration group, 10 μL for the transnasal administration group, 200 μL for the subcutaneous injection group, or one tape for the transdermal administration group, 10 times in total. One week after the 10th administration, the mouse serum was taken and the OVA-specific IgE titer in the serum was determined by ELISA.

The measurement method will be described in detail later.

TABLE 1

| | Allergen (dose) | Immuno-modulator (dose) | Support | Subject | Admin. site | Admin. conditions | IgE at $2^7$ dilution (ABS) |
|---|---|---|---|---|---|---|---|
| Reference Example 1 | none | none | none | BALB/c mouse | none | none | 2.00 |

TABLE 1-continued

| | Allergen (dose) | Immuno-modulator (dose) | Support | Subject | Admin. site | Admin. conditions | IgE at $2^7$ dilution (ABS) |
|---|---|---|---|---|---|---|---|
| Comparative Example 1 | OVA protein (10 μg) | none | Saline | BALB/c mouse | Sublingual | 10 times/ 2 weeks | 1.45 |
| Example 1 | OVA protein (10 μg) | Pantoea-derived LPS (1 μg) | Saline | BALB/c mouse | Sublingual | 10 times/ 2 weeks | 0.85 |
| Comparative Example 2 | OVA protein (10 μg) | none | Saline | BALB/c mouse | Transnasal | 10 times/ 2 weeks | 1.50 |
| Example 2 | OVA protein (10 μg) | Pantoea-derived LPS (1 μg) | Saline | BALB/c mouse | Transnasal | 10 times/ 2 weeks | 0.90 |
| Comparative Example 3 | OVA protein (10 μg) | none | pAANa tape | BALB/c mouse | Transdermal | 10 times/ 2 weeks | 1.90 |
| Example 3 | OVA protein (10 μg) | Pantoea-derived LPS (1 μg) | pAANa tape | BALB/c mouse | Transdermal | 10 times/ 2 weeks | 1.20 |
| Comparative Example 4 | OVA protein (10 μg) | none | Saline | BALB/c mouse | Subcutaneous injection | 10 times/ 2 weeks | 1.90 |
| Example 4 | OVA protein (10 μg) | Pantoea-derived LPS (1 μg) | Saline | BALB/c mouse | Subcutaneous injection | 10 times/ 2 weeks | 1.50 |

Examples 5 to 8, Comparative Examples 5 to 8

Vaccine compositions as shown in Table 2 were prepared by the procedure fundamentally similar to that in Examples 1 to 4 and Comparative Examples 1 to 4 except that a standardized allergen extract of Japanese cedar pollen for treatment (Torii Pharmaceutical Co., Ltd., 10 μg/mL) was used.

Five mice (8-week-old female BALB/C mice, Japan SLC, Inc.) per group were anesthetized and received the vaccine composition prepared in an amount of 20 μL for the sublingual administration group, 10 μL for the transnasal administration group, 200 μL for the subcutaneous injection group, or one tape for the transdermal administration group.

The preparations were prepared such that the standardized allergen extract of Japanese cedar pollen for treatment (10 μg/mL) and the *Pantoea agglomerans*-derived lipopolysaccharide solution (1 μg/mL) were administered per administration. Within two weeks from the above administration, each mouse was anesthetized and received the vaccine composition in an amount of 20 μL for the sublingual administration group, 10 μL for the transnasal administration group, 200 μL for the subcutaneous injection group, or one tape for the transdermal administration group, 10 times in total. One week after the 10th administration, the mouse serum was taken and the cedar pollen allergen extract-specific IgE titer in the serum was determined by ELISA.

The measurement method will be described in detail later.

TABLE 2

| | Allergen (dose) | Immuno-modulator (dose) | Support | Subject | Admin. site | Admin. conditions | IgE at $2^7$ dilution (ABS) |
|---|---|---|---|---|---|---|---|
| Reference Example 2 | none | none | none | BALB/c mouse | none | none | 1.90 |
| Comparative Example 5 | Cedar pollen extract dry powder (10 μg) | none | Saline | BALB/c mouse | Sublingual | 10 times/ 2 weeks | 1.70 |
| Example 5 | Cedar pollen extract dry powder (10 μg) | Pantoea-derived LPS (1 μg) | Saline | BALB/c mouse | Sublingual | 10 times/ 2 weeks | 1.01 |
| Comparative Example 6 | Cedar pollen extract dry powder (10 μg) | none | Saline | BALB/c mouse | Transnasal | 10 times/ 2 weeks | 1.66 |
| Example 6 | Cedar pollen extract dry powder (10 μg) | Pantoea-derived LPS (1 μg) | Saline | BALB/c mouse | Transnasal | 10 times/ 2 weeks | 1.20 |
| Comparative Example 7 | Cedar pollen extract dry powder (10 μg) | none | pAANa tape | BALB/c mouse | Transdermal | 10 times/ 2 weeks | 1.80 |

TABLE 2-continued

|  | Allergen (dose) | Immuno-modulator (dose) | Support | Subject | Admin. site | Admin. conditions | IgE at $2^7$ dilution (ABS) |
|---|---|---|---|---|---|---|---|
| Example 7 | Cedar pollen extract dry powder (10 μg) | Pantoea-derived LPS (1 μg) | pAANa tape | BALB/c mouse | Transdermal | 10 times/ 2 weeks | 1.11 |
| Comparative Example 8 | Cedar pollen extract dry powder (10 μg) | none | Saline | BALB/c mouse | Subcutaneous injection | 10 times/ 2 weeks | 1.88 |
| Example 8 | Cedar pollen extract dry powder (10 μg) | Pantoea-derived LPS (1 μg) | Saline | BALB/c mouse | Subcutaneous injection | 10 times/ 2 weeks | 1.50 |

Examples 9 to 12, Comparative Examples 9 to 12

Vaccine compositions as shown in Table 3 were prepared by the procedure fundamentally similar to that in Examples 1 to 4 and Comparative Examples 1 to 4 except that a mite allergen (Sigma-Aldrich, 10 μg/mL) was used.

Five mice (8-week-old female BALB/C mice, Japan SLC, Inc.) per group were anesthetized and received the vaccine composition prepared in an amount of 20 TL for the sublingual administration group, 10 μL for the transnasal administration group, 200 μL for the subcutaneous injection group, or one tape for the transdermal administration group. The preparations were prepared such that the mite allergen (10 μg/mL) and the *Pantoea agglomerans*-derived lipopolysaccharide solution (1 μg/mL) were administered per administration. Within two weeks from the above administration, each mouse was anesthetized and received the vaccine composition in an amount of 20 μL for the sublingual administration group, 10 μL for the transnasal administration group, 200 μL for the subcutaneous injection group, or one tape for the transdermal administration group, 10 times in total. One week after the 10th administration, the mouse serum was taken and the mite allergen-specific IgE titer in the serum was determined by ELISA.

The measurement method will be described in detail later.

TABLE 3

|  | Allergen (dose) | Immuno-modulator (dose) | Support | Subject | Admin. site | Admin. conditions | IgE at $2^7$ dilution (ABS) |
|---|---|---|---|---|---|---|---|
| Reference Example 3 | none | none | none | BALB/c mouse | none | none | 1.98 |
| Comparative Example 9 | Mite allergen (10 μg) | none | Saline | BALB/c mouse | Sublingual | 10 times/ 2 weeks | 1.40 |
| Example 9 | Mite allergen (10 μg) | Pantoea-derived LPS (1 μg) | Saline | BALB/c mouse | Sublingual | 10 times/ 2 weeks | 0.98 |
| Comparative Example 10 | Mite allergen (10 μg) | none | Saline | BALB/c mouse | Transnasal | 10 times/ 2 weeks | 1.36 |
| Example 10 | Mite allergen (10 μg) | Pantoea-derived LPS (1 μg) | Saline | BALB/c mouse | Transnasal | 10 times/ 2 weeks | 1.07 |
| Comparative Example 11 | Mite allergen (10 μg) | none | pAANa tape | BALB/c mouse | Transdermal | 10 times/ 2 weeks | 1.50 |
| Example 11 | Mite allergen (10 μg) | Pantoea-derived LPS (1 μg) | pAANa tape | BALB/c mouse | Transdermal | 10 times/ 2 weeks | 1.11 |
| Comparative Example 12 | Mite allergen (10 μg) | none | Saline | BALB/c mouse | Subcutaneous injection | 10 times/ 2 weeks | 1.70 |
| Example 12 | Mite allergen (10 μg) | Pantoea-derived LPS (1 μg) | Saline | BALB/c mouse | Subcutaneous injection | 10 times/ 2 weeks | 0.99 |

(Mouse Immunization Test)

The preparations were administered to 8-week-old female BALB/c mice 10 times within two weeks. One week after the final administration, the blood was taken from each mouse. The blood was centrifuged at 4° C. and 3000 G for 10 minutes, and 20 μL of the serum was mixed with 300 μL of a phosphate buffer (Nacalai Tesque, Inc.). Thereby, a serum sample was prepared.

The OVA-specific IgE titer in the mouse serum was determined, and thereby the immune tolerance induction was evaluated.

(Method of Measuring Antigen-Specific IgE Titer in Mouse Serum (ELISA))

First, 100-μL aliquots of the allergen (e.g., an OVA antigen solution for measurement of the OVA-specific IgE antibody titer) (100 μg/mL) diluted with a carbonate buffer were put into a 96-well plate for ELISA, and the system was left to stand overnight.

The wells were washed three times using PBS with Tween 20 (hereinafter, referred to as a washing buffer) prepared in advance, and 200-μL aliquots of a blocking solution prepared by diluting a blocking agent (Block Ace, DS Pharma Biomedical Co., Ltd.) with purified water to 4 g/400 mL were added thereto. The system was then left to stand for two hours at room temperature. Thereafter, the wells were washed three times using the washing buffer.

The serum sample was subjected to a two-fold serial dilution 15 times using a solution prepared by diluting a blocking agent (Block Ace, DS Pharma Biomedical Co., Ltd.) with a phosphate buffer (Nacalai Tesque, Inc.) to 0.4 g/100 mL (hereinafter, referred to as a reagent dilute solution). Then, 50-μL aliquots of this solution were added to the wells, and the system was left to stand for two hours at room temperature.

The wells were then washed three times using the washing buffer, and 100-μL aliquots of a 10,000 fold dilution prepared by diluting HRP-labelled anti-mouse IgE antibody (Goat-anti-mouse IgG Fc HRP, Bethyl Laboratories, Inc.) with the reagent dilute solution were added thereto. Thereafter, the system was left to stand for one hour at room temperature.

The wells were then washed three times using the washing buffer, and 100-μL aliquots of a TMB solution (ELISA POD TMB kit, Nacalai Tesque, Inc.) were added thereto. Thereto were added 100-μL aliquots of a 1 M sulfuric acid solution, and the resulting 96-well plate was subjected to measurement of the absorbance at 450 nm using a microplate reader (168-11135 CAM, Bio-Rad Laboratories, Inc.). Based on the absorbance during the serial dilutions, the maximum dilution factor at which the absorbance did not go under 0.1 was defined as the IgE titer in the mouse serum. This value was converted into a Log 2 value.

(Preparation of Allergy Mouse)

The allergen (OVA 10 μg/mL) and aluminum hydroxide gel (1 mg equivalent in terms of $Al(OH)_3$) were dissolved or suspended in a physiological saline solution to provide 200 μL of an injection. This injection was subcutaneously injected to a BALB/c mouse twice at an interval of one week. Further, the allergen was changed to cedar pollen (10 μg/mL) or an mite allergen (10 μg/mL) and allergy mice sensitized to the respective allergens were prepared in the same manner.

In each of the examples, the OVA-, allergen extract cedar pollen-, or mite allergen-specific IgE titer was reduced significantly. In the comparative examples, on the contrary, the reduction level was less significant.

These results demonstrate that combination use of an allergen and an immunomodulator which is a lipopolysaccharide derived from a specific gram-negative bacterium or a salt thereof is effective for induction of immune tolerance.

INDUSTRIAL APPLICABILITY

The allergy vaccine composition of the present invention contains a combination of at least one allergen with the aforementioned specific immunomodulator, and thus can safely effectively induce immune tolerance.

The invention claimed is:

1. A method of inducing immune tolerance to an allergen in a mammalian subject comprising administering to the subject a composition comprising a mixture of the allergen and an immunomodulator, wherein
   the allergen-specific IgE titer of the mammalian subject is reduced compared to the allergen-specific IgE titer induced in a corresponding mammalian subject administered with the allergen without the immunomodulator,
   the mass ratio of the total mass of the immunomodulator to the total mass of the allergen in the composition is in the range of 0.01 to 10;
   the immunomodulator is a lipopolysaccharide isolated from the gram-negative bacterium *Pantoea* or a salt of the lipopolysaccharide; and
   the allergen is a tree pollen selected from the group consisting of tree pollens from Acacia, Alder, Ash, American Beech, Birch, Box Elder, Mountain Cedar, Red Cedar, Cottonwood, Japanese Cypress, American Elm, Chinese Elm, Japanese Douglas fir, Sweetgum, *Eucalyptus*, Hackberry, Hickory, Linden, Sugar Maple, Mesquite, Mulberry, Oak, Olive, Pecan, Pepper Tree, Pine, Privet, Russian Olive, American Sycamore, Tree of Heaven, Walnut, and Black Willow.

2. The method according to claim 1, wherein the administration is transmucosal administration.

3. The method according to claim 2, wherein the administration is transnasal administration.

4. The method according to claim 1, comprising administering the composition to the subject once a month, two or more times.

5. The method according to claim 1, comprising administering the composition to the subject once every other week, two or more times.

6. The method according to claim 1, comprising administering the composition to the subject every day.

7. The method according to claim 1, wherein the subject is a human having an allergic disease.

8. The method according to claim 1, wherein the subject is a human not having an allergic disease.

9. The method according to claim 1, wherein the lipopolysaccharide is of *Pantoea agglomerans*.

* * * * *